United States Patent
Govari et al.

(10) Patent No.: US 8,357,149 B2
(45) Date of Patent: Jan. 22, 2013

(54) FILTER FOR SIMULTANEOUS PACING AND ABLATION

(75) Inventors: Assaf Govari, Haifa (IL); Andres Claudio Altmann, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 905 days.

(21) Appl. No.: 12/133,716

(22) Filed: Jun. 5, 2008

(65) Prior Publication Data

US 2009/0306641 A1 Dec. 10, 2009

(51) Int. Cl.
*A61B 18/12* (2006.01)

(52) U.S. Cl. ......................................... 606/34

(58) Field of Classification Search ............... 606/32–35
See application file for complete search history.

(56) References Cited

U.S. PATENT DOCUMENTS

| | | | |
|---|---|---|---|
| 5,443,489 A | 8/1995 | Ben-Haim | |
| 5,480,422 A | 1/1996 | Ben-Haim | |
| 5,954,665 A | 9/1999 | Ben-Haim | |
| 6,027,500 A * | 2/2000 | Buckles et al. | 606/34 |
| 6,113,592 A | 9/2000 | Taylor | |
| 6,669,692 B1 | 12/2003 | Nelson et al. | |
| 6,743,225 B2 | 6/2004 | Sanchez et al. | |
| 6,758,846 B2 * | 7/2004 | Goble et al. | 606/41 |
| 2003/0120271 A1 | 6/2003 | Burnside et al. | |
| 2007/0198007 A1 | 8/2007 | Govari et al. | |

OTHER PUBLICATIONS

"Band-Stop Filters" http://www.ecelab.com/band-stop.htm, copyright 2006.*
Carr, Joseph J. "Chapter 23: LC RF Filter Circuits." Secrets of RF Circuit Design. New York: McGraw-Hill, 2001.*
EP Search Report No. 09 25 1393 Dated Sep. 16, 2009.

* cited by examiner

*Primary Examiner* — Michael Peffley
*Assistant Examiner* — Daniel Fowler
(74) *Attorney, Agent, or Firm* — Louis J. Capezzuto

(57) ABSTRACT

Medical apparatus includes a pacing generator, which has first active and indifferent outputs and is configured to generate electrical pacing pulses between the first active and indifferent outputs for pacing a heart of a subject. A radio frequency (RF) generator has second active and indifferent outputs and is configured to generate RF electrical energy of a predetermined frequency between the second active and indifferent outputs for application to the heart of the subject simultaneously with the pacing pulses. A filter includes a first branch connected between the first and second active outputs and a second branch connected between the first and second indifferent outputs, each of the first and second branches including one or more notch filters having a high impedance in a vicinity of the frequency of the RF electrical energy.

11 Claims, 4 Drawing Sheets

FILTER FOR SIMULTANEOUS PACING AND ABLATION

FIELD OF THE INVENTION

The present invention relates generally to invasive cardiac therapies, and specifically to validating and monitoring percutaneous cardiac ablation procedures.

BACKGROUND OF THE INVENTION

Invasive cardiac ablation techniques for the treatment of arrhythmias are well known in the art. For example, U.S. Pat. Nos. 5,443,489 and 5,480,422, whose disclosures are incorporated herein by reference, describe systems for ablating cardiac tissue by application of radio-frequency (RF) energy to the tissue through a catheter.

In a cardiac ablation procedure, it is important to apply sufficient energy to create a lesion that will block undesired conduction, while minimizing collateral damage to surrounding tissues. Various methods have been proposed for monitoring ablation procedures for this purpose. For example, U.S. Pat. No. 6,743,225, whose disclosure is incorporated herein by reference, proposes to measure electrical activity of the cardiac tissue proximate a lesion site during an ablation treatment, and then to compare the measurements in order to determine whether the lesion is clinically efficacious so as to be able to block myocardial propagation. The electrical activity can include electrical signals corresponding to the local electrogram signal, pacing threshold value, and the like.

As another example, U.S. Patent Application Publication 2007/0198007, whose disclosure is incorporated herein by reference, describes methods and devices for monitoring intracardiac ablation progress in near real time, by evaluating capture of a pacing signal while ablation energy is concurrently directed to a target site. Sufficiency of ablation is indicated by failure of signal capture at a maximum predetermined pacing voltage. An electrode in a cardiac catheter is simultaneously used to test pacing capture and to deliver ablation energy.

SUMMARY OF THE INVENTION

Notwithstanding the above-mentioned references, safety concerns have led practitioners to avoid applying pacing and RF ablation energy to the heart simultaneously, mainly due to the possibility of leakage of substantial RF power into the pacing circuit. Embodiments of the present invention that are described hereinbelow overcome this problem by using a novel array of notch filters to keep RF energy from penetrating through the pacing circuit. The array comprises two branches of notch filters with high impedance in the frequency range that is used for ablation: one branch protecting the signal path between the pacing circuit and the catheter tip, and the other protecting the return path. The filters have low impedance at the pacing frequency, thus permitting pacing to proceed simultaneously with ablation.

There is therefore provided, in accordance with an embodiment of the present invention, medical apparatus, including:

a pacing generator, which has first active and indifferent outputs and is configured to generate electrical pacing pulses between the first active and indifferent outputs for pacing a heart of a subject;

a radio frequency (RF) generator, which has second active and indifferent outputs and is configured to generate RF electrical energy of a predetermined frequency between the second active and indifferent outputs for application to the heart of the subject simultaneously with the pacing pulses; and a filter including a first branch connected between the first and second active outputs and a second branch connected between the first and second indifferent outputs, each of the first and second branches including one or more notch filters having a high impedance in a vicinity of the frequency of the RF electrical energy.

In some embodiments, the apparatus includes a catheter, which includes a distal tip that is configured to be inserted into a chamber of the heart and an electrode at the distal tip, wherein the first and second active outputs are coupled together to deliver the pacing pulses and the RF electrical energy to the heart via the electrode. Additionally or alternatively, the apparatus includes a monitor, which is configured to detect capture of the pacing pulses by the heart during application of the RF electrical energy.

In some embodiments, each of the first and second branches includes a plurality of notch filters having respective notch frequencies in the vicinity of the frequency of the RF electrical energy. In a disclosed embodiment, each of the notch filters includes an inductor and a capacitor arranged in parallel.

Additionally or alternatively, the filter includes a third branch, which is connected between the first and second branches and the first active and indifferent outputs and which includes a further one or more notch filters that have a low impedance in the vicinity of the frequency of the RF electrical energy. The further one or more notch filters may include a plurality of notch filters including an inductor and a capacitor arranged in series and having respective notch frequencies in the vicinity of the frequency of the RF electrical energy. Further additionally or alternatively, the filter includes a common mode choke connected between the third branch and the first active and indifferent outputs.

There is also provided, in accordance with an embodiment of the present invention, a method for treating a heart of a subject, the method including:

operating a pacing generator, which has first active and indifferent outputs, to generate electrical pacing pulses between the first active and indifferent outputs so as to pace the heart;

actuating a radio frequency (RF) generator, which has second active and indifferent outputs, to generate RF electrical energy of a predetermined frequency between the second active and indifferent outputs for application to the heart simultaneously with the pacing pulses;

inhibiting penetration of the RF electrical energy into the pacing generator by connecting a first branch of a filter between the first and second active outputs and a second branch of the filter between the first and second indifferent outputs, each of the first and second branches including one or more notch filters having a high impedance in a vicinity of the frequency of the RF electrical energy; and simultaneously applying the pacing pulses and the RF electrical energy to the heart.

The present invention will be more fully understood from the following detailed description of the embodiments thereof, taken together with the drawings in which:

DETAILED DESCRIPTION OF EMBODIMENTS

Figure 1:
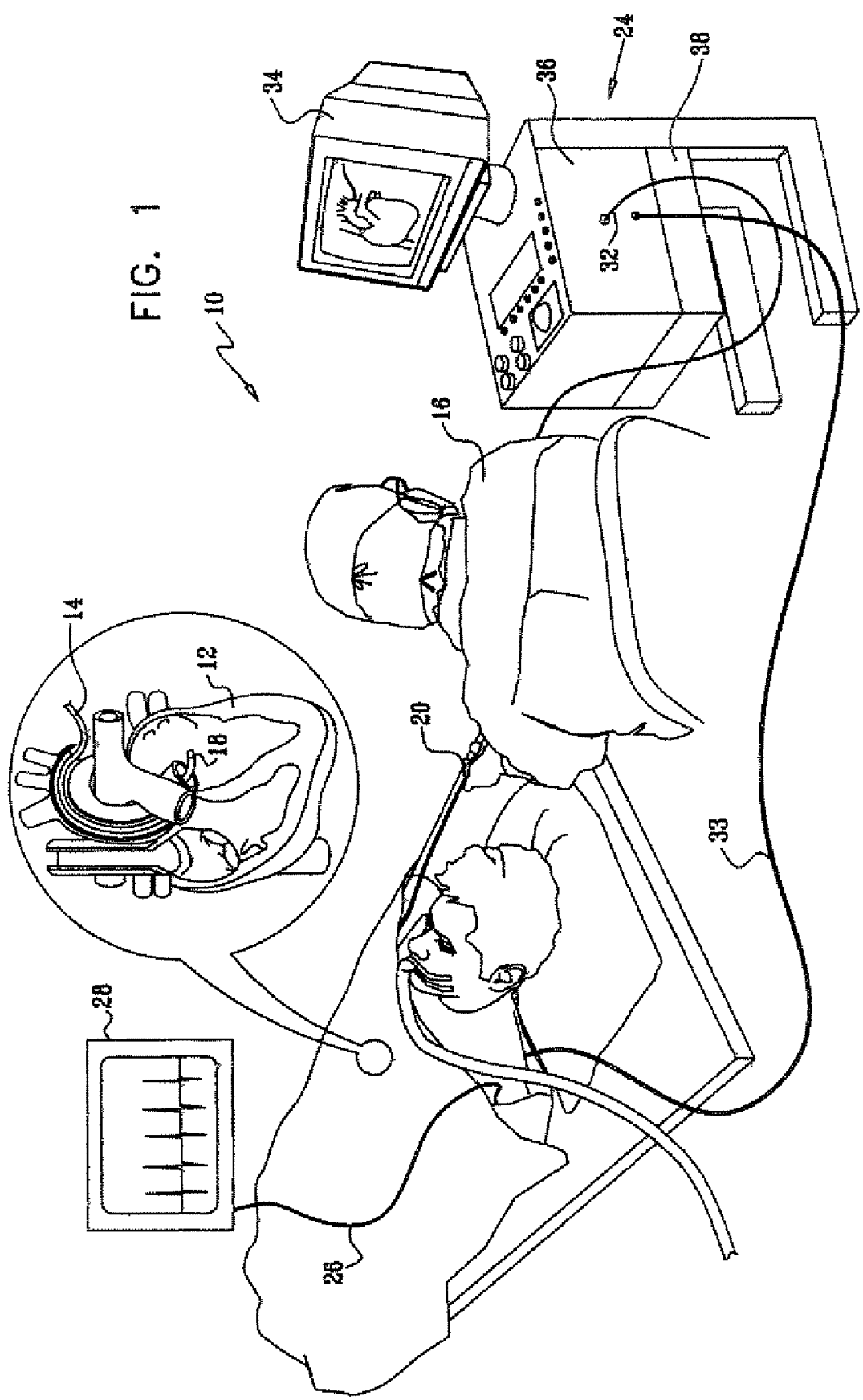
FIG. 1 is a schematic, pictorial illustration showing a system for percutaneous ablation therapy in the heart of a subject, in accordance with an embodiment of the present invention.

FIG. 1 is a schematic, pictorial illustration of a system 10 for performing ablative procedures on a heart 12 of a living subject, in accordance with a disclosed embodiment of the invention. The system comprises a probe, typically a catheter 14, which is percutaneously inserted by an operator 16, who is typically a physician, through the patient's vascular system into a chamber or vascular structure of the heart. Operator 16 brings a distal tip 18 of the catheter into contact with the heart wall at a target site that is to be ablated. RF electrical current is then conducted through wires in the catheter to one or more electrodes at distal tip 18, which apply the RF energy to the myocardium. The energy is absorbed in the tissue, heating it to a point (typically about 50° C.) at which it permanently loses its electrical excitability. When successful, this procedure creates non-conducting lesions in the cardiac tissue, which can disrupt abnormal electrical pathways that cause arrhythmias.

Catheter 14 typically comprises a handle 20, having suitable controls to enable operator 16 to steer, position and orient distal tip 18 of the catheter as desired during the ablation. To aid operator 16 in positioning the catheter, the distal portion of the catheter may contains position sensors (not shown) that provide signals to a positioning processor located in a console 24. Catheter 14, may be adapted, mutatis mutandis, from ablation catheters that are known in the art, such as the catheters described in U.S. Pat. No. 6,669,692, whose disclosure is incorporated herein by reference. ECG electrodes (not shown) on the patient's body surface conduct electrical signals via a cable 26 to an ECG monitor 28 (which may also be integrated into console 24). A user interface 34 provides feedback to the operator and permits the operator to adjust system functions as appropriate.

Embodiments of the present invention combine simultaneous ablation and pacing so that an ablation lesion can be assessed in real time, without interrupting the ablation procedure. Console 24 includes a RF power source 36 that generates an ablation power signal, which is conveyed to catheter 14 via a cable 32. The RF power may be generated at any suitable frequency, but around 500 kHz is typical. A ground cable 33 provides a return path (typically via a back pad or other skin-surface electrode). Alternatively, the RF power may be delivered in a bipolar mode, whereby catheter 14 provides the return path, as well.

Console 24 also comprises a low-frequency pacing generator 38 that produces a cardiac pacing signal. Pacing generator 38 typically comprises circuitry for varying its output voltage under control of the operator 16, for example, from 3 to 6 volts, while maintaining a constant current output. Alternatively, pacing generator 38 may maintain a constant voltage, while varying its current output or may permit both the voltage and the current to be adjusted. RF power source 36 and pacing generator 38 are both coupled to catheter 14 via cable 32 and to the return path provided by cable 33.

Figure 2:
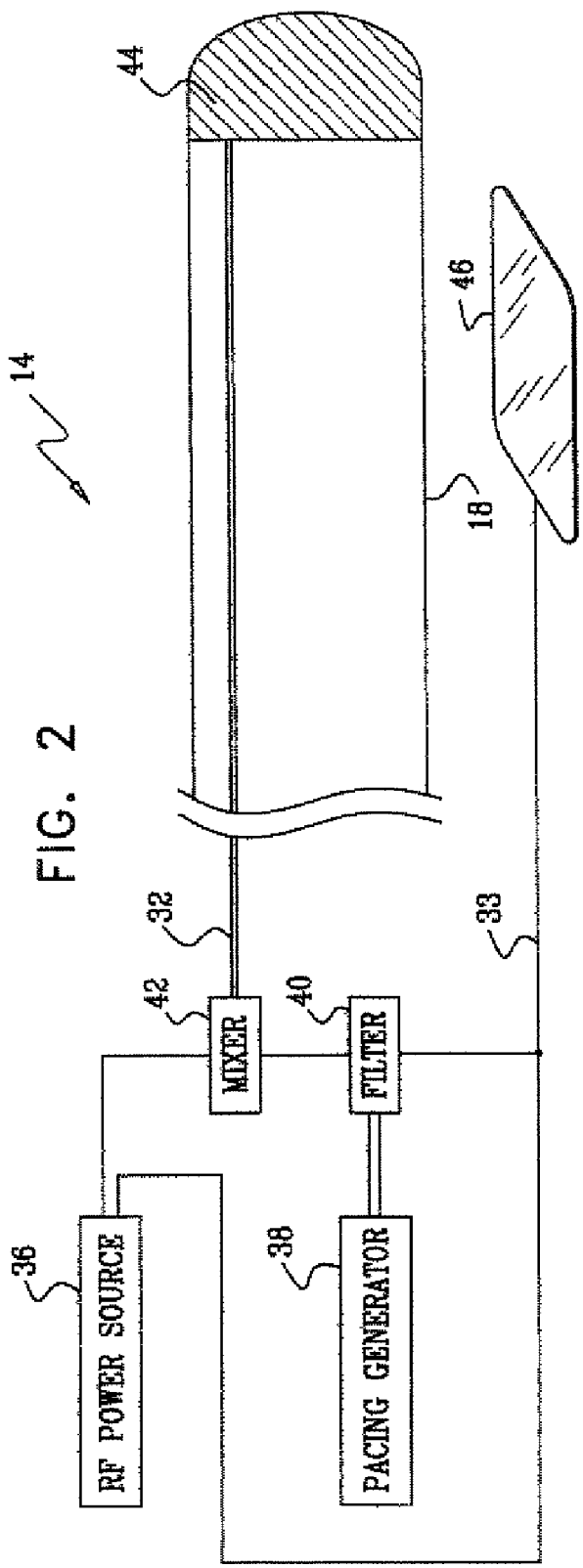
FIG. 2 is a block diagram that schematically shows circuitry for delivering RF ablation and pacing signals to a catheter electrode, in accordance with an embodiment of the present invention.

FIG. 2 is a block diagram that schematically shows distal tip 18 of catheter 14 and associated circuitry in console 24, in accordance with an embodiment of the present invention. The output of pacing generator 38, including both the active and return connections, is connected to a filter 40, which is shown in detail in the figures that follow. The purpose of this filter is to prevent leakage of RF energy from RF power source 36 into the pacing circuits, as well as blocking direct current return from the pacing generator to the catheter during ablation. (These features of the filter are very important for patient safety and address concerns that have contraindicated the use of simultaneous ablation and pacing in the past.) The output of RF power source 36 is mixed with the pacing signal following filter 40 in a mixer 42, which may comprise any suitable type of high-frequency electrical junction that is known in the art. The combined RF and pacing waveform is conducted by cable 32 through catheter 14 and is applied to a common electrode 44 at distal tip 18 of the catheter. The combined waveform simultaneously paces the patient's heart and delivers ablation energy to the target.

An "indifferent" electrode 46 is connected to cable 33 as the return path for both the RF and pacing currents. Electrode 46 may typically comprise a back pad or other skin-surface electrode, as noted above. Alternatively, the RF power source and pacing generator may have separate indifferent electrodes and return paths (not shown).

Although electrode 44 is shown in FIG. 2 as a single unit, catheter 14 may alternatively comprise any number of electrodes in any form. For example, the catheter may comprise two or more ring electrodes, a plurality or array of point electrodes, or any combination of these types of electrodes for performing the therapeutic functions described herein. Although it is advantageous for pacing generator 38 and RF power source 36 to be connected to the same electrode 44 via mixer 42, as shown in the figures, catheter 14 may alternatively comprise separate pacing and RF electrodes (typically in close proximity to one another), which are driven separately by the pacing generator and RF power source. Even in this latter configuration, the isolation provided by filter 40 is important when ablation and pacing go on simultaneously.

During the ablation procedure, ECG monitor 28 (FIG. 1) indicates whether the heart has actually captured the pacing signal, i.e., whether the heartbeat synchronizes with the pacing signal applied through electrode 44. As long as the pacing signal is captured, lesion formation is considered to be incomplete. The pacing amplitude may be increased gradually during the ablation procedure, as the pacing threshold increases due to lesion formation. When the pacing signal can no longer be captured even at high amplitude, lesion formation is considered to be complete, and the procedure at the current ablation site is terminated. In general, the pacing threshold increases with the size of the lesion, and this technique may thus be used to control the size of the lesion that is created by ablation. Additional lesions may then be ablated at other locations, depending on the therapeutic plan.

This sort of pacing-based ablation technique is described in greater detail in the above-mentioned U.S. Patent Application Publication 2007/0198007, which also describes variations and additions to the technique that may be combined with the embodiments of the present invention that are described herein.

Figure 3:
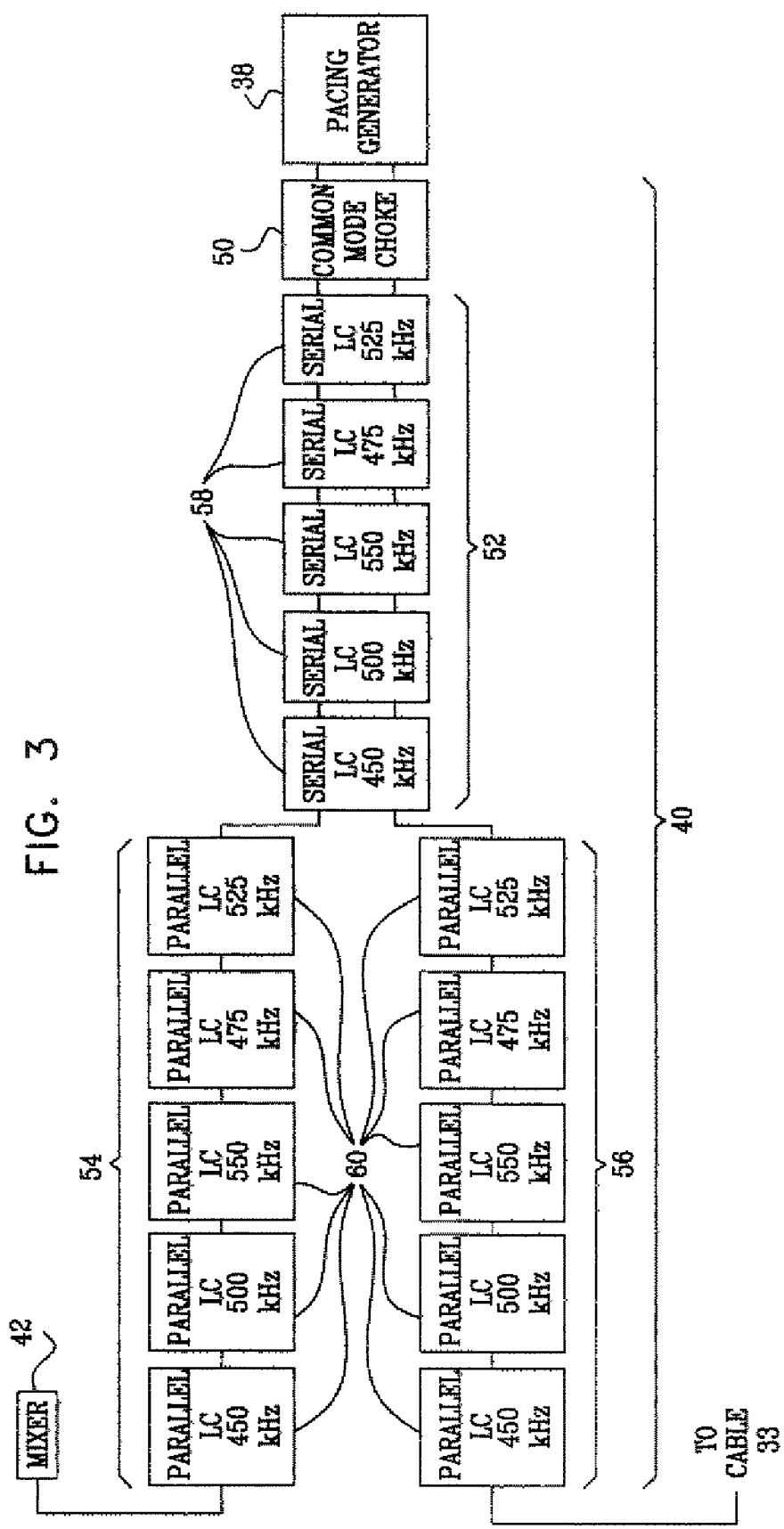
FIG. 3 is a block diagram that schematically shows a filter circuit for use in simultaneous RF ablation and pacing of the heart, in accordance with an embodiment of the present invention.
Figure 4:
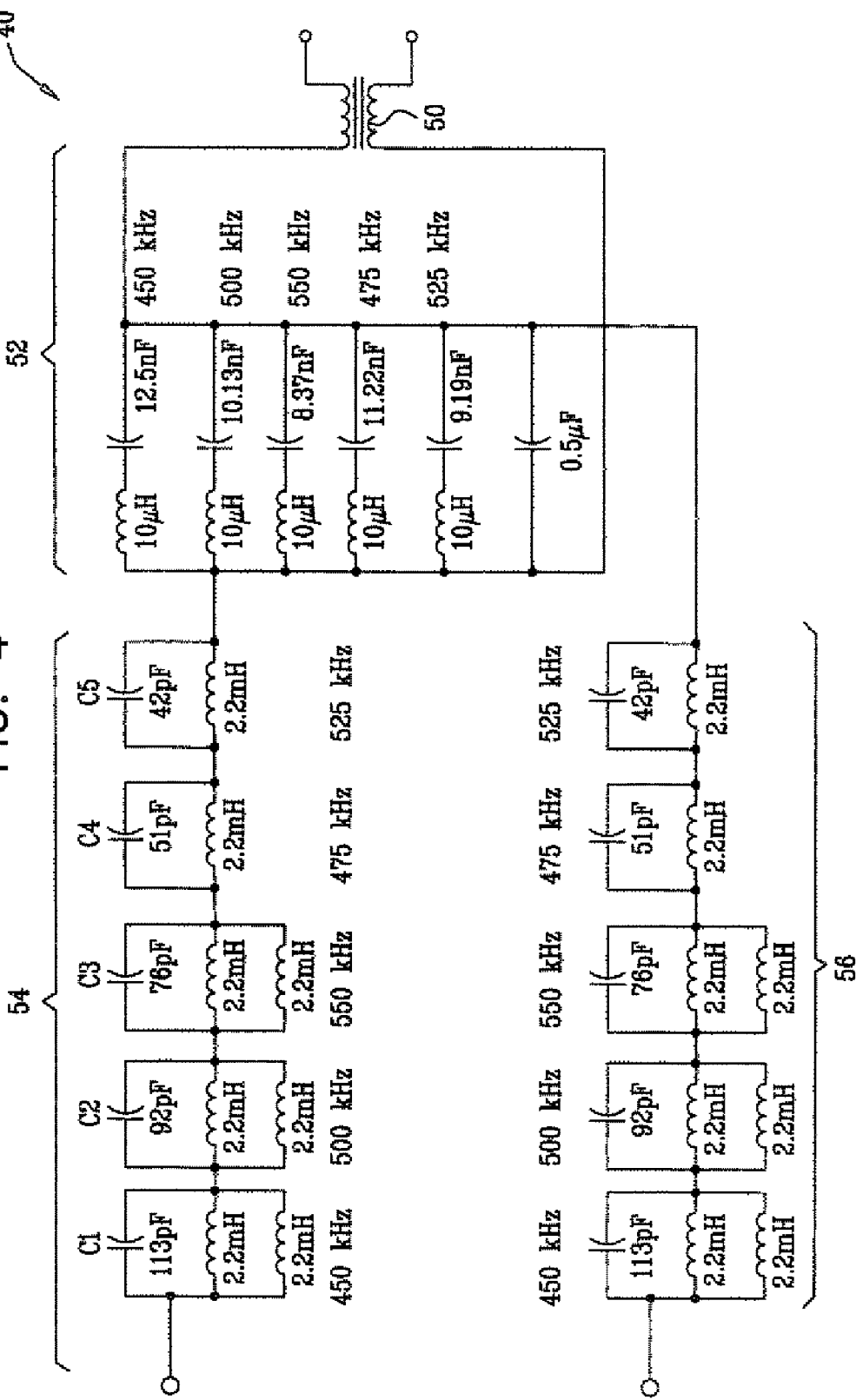
FIG. 4 is a schematic circuit diagram showing details of a filter circuit for use in simultaneous RF ablation and pacing of the heart, in accordance with an embodiment of the present invention.

Reference is now made to FIGS. 3 and 4, which schematically show details of filter 40, in accordance with an embodiment of the present invention. FIG. 3 is a block diagram that shows the overall architecture of the filter, while FIG. 4 is a circuit diagram showing details of a particular implementation of this architecture.

Filter 40 has the following features:

Two branches 54 and 56 of parallel notch filter blocks 60. Each block is a passive unit comprising an inductor and capacitor connected in parallel. These blocks have high impedance in the frequency range close to the specified resonant frequency of RF ablation. In the example shown in the figures, the component values of the inductors and capacitors are chosen so as to create multiple, overlapping notches, spaced 25 kHz apart over a range of ±50 kHz around the 500 kHz center frequency.

A branch 52 of serial notch filter blocks 58. Each block is a passive unit with a serially-connected inductor and capacitor. These blocks have low impedance in the frequency range close to the specified resonant frequency and thus shunt to ground any RF energy that penetrated through branches 54 and 56. Here, too, blocks 58 create multiple, overlapping notches, spaced 25 kHz apart over a range of ±50 kHz around the 500 kHz center frequency.

A common mode choke 50 attenuates any small common-mode noise that would otherwise pass to the pacer side of filter 40.

Of the two branches of parallel blocks 60, branch 54 connects via mixer 42 to electrode 44 at the tip of catheter 14, while branch 56 connects to indifferent electrode 46. Thus, these blocks separate not only the energetic catheter tip electrode from pacing generator 38, but also the return path. On the other hand, for the low-frequency pacing pulses from the pacing generator, parallel blocks 60 and common mode choke 50 have low impedance, so pacing is enabled. Combining the parallel and serial blocks as shown in the figures creates strong energy attenuation (and isolation) in the frequency range of 500 kHz. Alternatively, the notch filters may be designed for other frequency ranges, and larger or smaller numbers of the filter blocks may be used, depending on the ablation parameters and the required degree of attenuation.

RF power source 36 typically includes an impedance measurement circuit (not shown), which checks the impedance of the RF circuit through the patient's body to ensure that there is good electrical contact before the high-power RF ablation current is actuated. Because branches 54 and 56 connect to both the active and indifferent electrodes, filter 40 will not affect the impedance measurement.

Although the embodiment described above relates specifically to combination of pacing with RF ablation therapy, the principles of the present invention may likewise be applied in any sort of diagnostic or therapeutic environment in which RF energy is applied to the body simultaneously with pacing of the heart. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Medical apparatus for safely administering contraindicated simultaneous ablation and pacing in a heart of a subject, comprising:
    a pacing generator, which has first active and indifferent outputs and is configured to generate electrical pacing pulses between the first active and indifferent outputs for pacing a heart of a subject;
    a radio frequency (RF) generator, which has second active and indifferent outputs and is configured to generate RF electrical energy of a predetermined frequency between the second active and indifferent outputs for applying ablation to the heart of the subject simultaneously with the pacing pulses;
    a filter comprising a first branch connected between the first and second active outputs and a second branch connected between the first and second indifferent outputs, each of the first and second branches comprising one or more notch filters having a high impedance in a vicinity of the frequency of the RF electrical energy and wherein the filter comprises a third branch, which is connected between the first and second branches and the first active and indifferent outputs and which comprises a further one or more notch filters that have a low impedance in the vicinity of the frequency of the RF electrical energy, wherein the filter prevents leakage of RF energy from the RF generator into the pacing generator; and
    a mixer for combining the first active and indifferent outputs with the second active and indifferent outputs and forming a combined RF and pacing waveform for delivering contraindicated simultaneous ablation and pacing in the heart of the subject.

2. The apparatus according to claim 1, and comprising a catheter, which comprises a distal tip that is configured to be inserted into a chamber of the heart and an electrode at the distal tip, wherein the first and second active outputs are coupled together to deliver the pacing pulses and the RF electrical energy to the heart via the electrode.

3. The apparatus according to claim 1, and comprising a monitor, which is configured to detect capture of the pacing pulses by the heart during application of the RF electrical energy.

4. The apparatus according to claim 1, wherein each of the first and second branches comprises a plurality of notch filters having respective notch frequencies in the vicinity of the frequency of the RF electrical energy.

5. The apparatus according to claim 4, wherein each of the notch filters comprises an inductor and a capacitor arranged in parallel.

6. The apparatus according to claim 1, wherein the further one or more notch filters comprise a plurality of notch filters comprising an inductor and a capacitor arranged in series and having respective notch frequencies in the vicinity of the frequency of the RF electrical energy.

7. The apparatus according to claim 1, wherein the filter comprises a common mode choke connected between the third branch and the first active and indifferent outputs.

8. A method for treating a heart of a subject with safely administered contraindicated simultaneous ablation and pacing, the method comprising:
    operating a pacing generator, which has first active and indifferent outputs, to generate electrical pacing pulses between the first active and indifferent outputs so as to pace the heart;
    actuating a radio frequency (RF) generator, which has second active and indifferent outputs, to generate RF electrical energy of a predetermined frequency between the second active and indifferent outputs for applying ablation to the heart simultaneously with the pacing pulses;
    inhibiting penetration of the RF electrical energy into the pacing generator by connecting a first branch of a filter between the first and second active outputs and a second branch of the filter between the first and second indifferent outputs, each of the first and second branches comprising one or more notch filters having a high impedance in a vicinity of the frequency of the RF electrical energy, and connecting a third branch, which is connected between the first and second branches and the first active and indifferent outputs and which comprises a further one or more notch filters that have a low impedance in the vicinity of the frequency of the RF electrical energy and wherein the filter prevents leakage of RF energy from the RF generator into the pacing generator;

combining the first active and indifferent outputs with the second active and indifferent outputs and forming a combined RF and pacing waveform; and simultaneously applying the combined RF and pacing waveform for contraindicated pacing pulses and the RF electrical energy to the heart.

9. The method according to claim 8, wherein simultaneously applying the pacing pulses comprises inserting a distal tip of a catheter into a chamber of the heart so that the distal tip contacts a tissue of the heart, and conveying the pacing pulses and the RF electrical energy to an electrode at the distal tip.

10. The method according to claim 8, wherein applying the RF electrical energy comprises creating a lesion in the heart by ablating a tissue in the heart, and wherein the method comprises assessing the lesion by detecting capture of the pacing pulses by the heart during application of the RF electrical energy.

11. The method according to claim 8, wherein each of the first and second branches comprises a plurality of notch filters having respective notch frequencies in the vicinity of the frequency of the RF electrical energy.

* * * * *